(12) United States Patent
Warmington et al.

(10) Patent No.: US 6,916,626 B1
(45) Date of Patent: Jul. 12, 2005

(54) DETECTION OF CANDIDA

(75) Inventors: John Warmington, Willetton (AU); Denis Ballantyne, Kewdale (AU)

(73) Assignee: Rockeby biomed Ltd., Bentley (AU)

( * ) Notice: Subject to any disclaimer, the term of this patent is extended or adjusted under 35 U.S.C. 154(b) by 244 days.

(21) Appl. No.: 09/841,188

(22) Filed: Apr. 25, 2001

(51) Int. Cl.[7] ............................ G01N 33/53; C12Q 1/68; C12Q 1/32; C12P 19/34

(52) U.S. Cl. ............................ 435/7.31; 435/6; 435/26; 435/91.1

(58) Field of Search .......................... 435/7.31, 6, 26, 435/91.1

(56) References Cited

U.S. PATENT DOCUMENTS

| | | | | |
|---|---|---|---|---|
| 4,806,465 A | * | 2/1989 | Buckley et al. | 435/7 |
| 5,545,525 A | | 8/1996 | Montplaisir et al. | |
| 5,766,874 A | * | 6/1998 | Miyada et al. | 435/26 |

OTHER PUBLICATIONS

Ballantyne et al. "Purification of native enolase from medically important *Candida* species" Biotechnology and Applied Biochemistry, vol. 31, pp. 213–218, 2000.*

A. L. Sinclair et al., "A Rapid enzyme–linked immunosorbent assay (ELISA) for lgG ntibodies to *Candida–albicans*: preliminary studies in duodenal Ulcer Patients", Medical Laboratory Sciences, 1987, vol. 44, pp. 137–140.

Denis S. Ballantyne et al., "Purification of native enolase from medically important *Candida* species", Biotechnology and Applied Biochemistry, 2000, vol. 31, No. 3, pp. 213–218.

Rae Ellen Syverson et al., "Increasing the Predictive Value Positive of the Precipitin Test for the Diagnosis of Deep Seated Candidiasis", American Journal of Clinical Pathology, 1978, vol. 70, No. 5, pp. 826–831, published by American Society of Clinical Pathologists.

Nancy A. Strockbine et al., "Identification and Molecular Weight Characterization of Antigens from *Candida albicans* that are Recognized by Human Sera", Infection and Immunity, Feb. 1984, vol. 43, No. 2, pp. 715–721; published by American Society for Microbiology.

Louis de Repentigny, "Serodiagnosis of Candidiasis Aspergillosis and Cryptococcosis", Clinical Infectious Diseases, 1992, vol. 14, No. Suppl. 1, pp. S11–S22.

* cited by examiner

*Primary Examiner*—Rodney P Swartz
*Assistant Examiner*—Khatol S Shahnan-Shah
(74) *Attorney, Agent, or Firm*—Foley & Lardner LLP

(57) ABSTRACT

The present invention relates to a method and a means of diagnosing *Candida* infection. In particular, the present invention relates to a method of diagnosing *Candida* infection comprising the steps of obtaining a biological sample from a subject at risk of, or suspected to be suffering from, *Candida* infection, contacting the sample with a mannose depleted antigen composition comprising a soluble cytoplasmic antigen preparation comprising antigens of molecular weight 55 kDa, 30 kDa and 20 kDa and detecting the antigen/antibody reaction.

20 Claims, 7 Drawing Sheets

(3 of 7 Drawing Sheet(s) Filed in Color)

DETECTION OF CANDIDA

FIELD OF THE INVENTION

The present invention relates to a method and a means of diagnosing *Candida* infection. In particular the present invention relates to a method of diagnosing *Candida* infection which is both sensitive and rapid.

BACKGROUND OF THE INVENTION

*Candida* is the most commonly identified causative agent of oral or vaginal thrush. However, over the last few decades *Candida* has emerged as a significant cause of life-threatening infections in hospital patients. Ironically the increasing incidence of these "invasive" or "systemic" *Candida* infections has been advances in modern medicine. Patients that are now surviving major injuries, surgery, cancers and organ transplants are vulnerable to life-threatening *Candida* infections. In the United States, *Candida* is now the forth most common cause of blood infections in hospitals.

The major problem with systemic *Candida* infections is that there are few definitive clinical signs or symptoms. Treatment is largely based on suspicion rather than a definitive diagnosis. Even with the availability of anti-fungal drugs such as fluconazole a high mortality rate (30 to 70%) is associated with systemic *Candida* infections. The high rate of mortality is largely due to the rapid onset of infection and a rapidly fatal outcome. Without an accurate diagnosis the infection often goes unnoticed until it is too late to effectively treat. This has led to a comment by clinicians that *Candida* infections are usually diagnosed at autopsy. Accordingly, there is a need for a rapid diagnostic assay that is capable of early diagnosis of *Candida* infection so that appropriate treatment may be instituted thereby reducing the mortality rate.

The main difficulty in the diagnosis of *Candida* infections is that being a commensal, mere isolation of *Candida* from body surfaces, or orifices, is not diagnostic of an infection. Culture of *Candida* from blood or deep tissue is still the main method of diagnosis of systemic *Candida* infections. However, it can take several days for a culture to become positive, by then it may be too late to effectively treat the infection. Also, false positives may occur due to contamination from superficial body sites. Of more importance, is the observation that in up to fifty percent of autopsy proven cases of systemic candidiasis, blood cultures were negative and therefore of no diagnostic value.

Nuclear magnetic resonance (NMR) and radioisotope scanning have been used to detect *Candida* infections in tissues and organs. However, those methods are not useful for early diagnosis.

Recently analysis of the *Candida* metabolite arabinitol was proposed as a diagnostic tool. However, as arabinitol is produced by the human body, further clinical studies have cast doubt on its value.

The polymerase chain reaction (PCR) has also been used in the diagnosis of invasive *Candida* infections. However, PCR has not established itself as a useful diagnostic method for *Candida* for the same reasons as outlined above ie *Candida* is a ubiquitously present microorganism and false positives, due to superficial contamination, are prevalent.

Immunoassays are the established procedures for the diagnosis of many types of infectious diseases. Immunoassays have the advantage that they are rapid and have a standardised assay format. Immunoassays can be designed to either detect *Candida* antigens, or host antibodies reactive against *Candida* antigens. Several immunoassays are commercially available for the detection of *Candida* antigens in sera or other body fluids. However, these assays lack either sensitivity or specificity or both.

Immunoassays have been developed based on the detection of immunodominant *Candida* antigens. *Candida* mannan is a highly immunogenic cell wall antigen. However, as *Candida* is a commensal, most individuals have antibody to *Candida* mannan, so its usefulness in the diagnosis of systemic infection is limited. The applicant has now surprisingly found that a more discriminatory assay for *Candida* than previously used is the detection of cytoplasmic antigen. The advantage of this diagnostic assay is that antibody to this cytoplasmic antigen is only produced in response to an actual infection. The applicant has further demonstrated that the use of a combination of cytoplasmic antigens with other antigens is very predicative of *Candida* infection.

Accordingly, the present invention overcomes or at least alleviates the problems normally associated with diagnosing *Candida* infection.

SUMMARY OF THE INVENTION

In its most general aspect, the invention disclosed herein provides a simple and rapid method for diagnosis of *Candida* infection. The method of diagnosis of *Candida* infection may be used to screen large numbers of samples for possible infection.

Accordingly, in one aspect, the invention provides a method of diagnosing *Candida* infection, comprising the steps of:

a). obtaining a biological sample from a subject at risk of, or suspected to be suffering from, *Candida* infection, and b). measuring the levels of antibody to *Candida* cytoplasmic antigen present in the biological sample.

Antibody levels may be measured using known techniques of immunology including enzyme-linked immunoassay (ELISA or EIA), biligand binding (sandwich technique), fluorometric assay, chemiluminescent assay, radialimmunodiffusion or radioimmunoassay (RIA). ELISA or chemiluminescent assay methods are particularly preferred, since these are quick, sensitive, and specific, and are readily automated for large-scale use. These methods also provide quantitative determinations.

The diagnostic method utilises antigens expressed by *Candida*, especially cytoplasmic antigen. The antigens isolated from *Candida* as disclosed herein may, in certain embodiments of the diagnostic method of the present invention, be immobilised on an inert surface, embedded in a gel, or may be conjugated to a molecule which imparts colour, fluorescence or radioactivity to the antigen.

In a second aspect, the invention provides a method for assessing the prognosis of *Candida* infection, comprising the steps of measuring the levels of antibody to *Candida* cytoplasmic antigen in a biological sample.

Persons skilled in the art will appreciate that the techniques disclosed herein may be used on any type of biological sample. Preferable the biological sample is selected from the group consisting of bone marrow, plasma, spinal fluid, lymph fluid, the external sections of the skin from respiratory, intestinal, and genitourinary tracts, tears, saliva, milk, blood; both whole blood and sera, blood cells, tumours and organs. Most preferably the biological sample is sera.

Biological samples that may be analysed by the method of the present invention can also be obtained via swabs, shunts or the like. The biological samples may be analysed directly, or may be treated prior to testing by, for example, concentration or pH adjustment.

In a third aspect, the present invention further provides a method of detecting the presence or absence of a *Candida* antibody comprising the steps of:

a). exposing a biological sample, which may include a *Candida* antibody, to an isolated cytoplasmic *Candida* antigen; and b). detecting the reaction between antibody and antigen.

In an especially preferred embodiment of the present invention the diagnostic assay further utilises other *Candida* antigens in combination with the cytoplasmic antigen. In particular the cell wall antigen (including mannose) and/or purified immunodominant antigen (enolase) are utilised.

Accordingly, in a forth aspect of the present invention there is provided a method of diagnosing *Candida* infection, comprising the steps of:

a). obtaining a biological sample from a subject at risk of, or suspected to be suffering from, *Candida* infection, and b). measuring the levels of antibody present in the biological sample to *Candida* cytoplasmic antigen in combination with measuring the levels of antibody to either cell wall antigen or immunodominant antigen (enolase) or both.

The reagents and means of diagnosis of the present invention may also be embodied in a kit for use in a diagnostics laboratory or may be adapted and automated for analysing large numbers of samples at a central receiving centre.

Accordingly, in a fifth aspect the invention provides a kit when used for detecting the presence or absence of a *Candida* antibody in a biological sample, comprising:

a). a biological sample collection device;

b). a cytoplasmic *Candida* antigen; and c). means for detecting reaction between the antibody and antigen in the sample.

Suitable buffering agents and ionic salts may also be included in the kit.

In a sixth aspect the invention provides a method of preparing a cytoplasmic antigen comprising the step of removing lipoproteins by chloroform extraction.

BRIEF DESCRIPTION OF THE FIGURES

The application contains at least one drawing executed in color. Copies of this patent or patent application publication with color drawing(s) will be provided by the Office upon request and payment of the necessary fee.

ABBREVIATIONS USED

Figure 1:
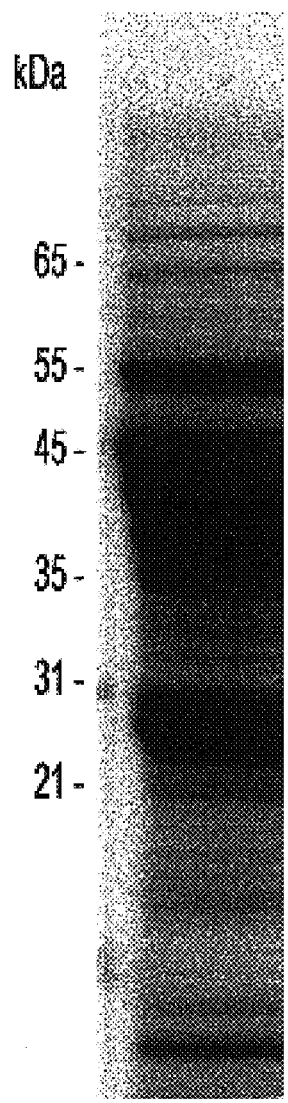
FIG. 1 shows a coomassie blue stained SDS-PAGE with major protein bands of the *Candida* cytoplasmic antigen fraction observed at 55 kDa, 35 to 45 kDa region, 30 kDa and 20 kDa.

EDTA Ethylenediaminetetraacetic acid
EIA Enzyme immunoassay
ELISA Enzyme-linked immunosorbent assay
RIA Radioimmunoassay
BSA Bovine serum albumin
DMSO Dimethyl sulfoxide
β-Me β-mercaptoethanol
TMB 3,3', 5,5'-tetramethyl-benzidine

DETAILED DESCRIPTION OF THE PREFERRED EMBODIMENTS

The practice of the present invention employs, unless otherwise indicated, conventional molecular biology, cellular biology, and immunoassay techniques within the skill of the art. Such techniques are well known to the skilled worker, and are explained fully in the literature. See, e.g., Harlow and Lane, "Antibodies: A Laboratory Manual" (1988); Maniatis, Fritsch & Sambrook, "Molecular Cloning: A Laboratory Manual" (1982); "Animal Cell Culture" (R. I. Freshney, ed., 1986); "Immobilised Cells and Enzymes" (IRL Press, 1986); B. Perbal, "A Practical Guide to Molecular Cloning" (1984); Sambrook, et al., "Molecular Cloning: a Laboratory Manual" (1989) and Ausubel, F. et al., 1989–1999, "Current Protocols in Molecular Biology" (Green Publishing, New York).

In describing the present invention, the following terminology is used in accordance with the definitions set out below.

As used herein, a "biological sample" refers to a sample of tissue or fluid isolated from a individual, including but not limited to bone marrow, plasma, serum, spinal fluid, lymph fluid, the external sections of the. skin, respiratory, intestinal, and genitourinary tracts, tears, saliva, milk, blood; both whole blood and anti-coagulated whole blood, blood cells, tumours, organs, and also includes samples of in vivo cell culture constituents, including but not limited to conditioned medium resulting from the growth of cells in cell culture medium, putatively *Candida* infected cells, recombinant cells, and cell components.

"Human tissue" is an aggregate of human cells which may constitute a solid mass. This term also encompasses a suspension of human cells, such as blood cells, or a human cell line.

For the purposes of this specification it will be clearly understood that the word "comprising" means "including but not limited to", and that the word "comprises" has a corresponding meaning.

It will be clearly understood that, although a number of prior art publications are referred to herein, this reference does not constitute an admission that any of these documents forms part of the common general knowledge in the art, in Australia or in any other country.

Persons skilled in the art will appreciate that any number of different immunoassays may be used in the present invention. For example, the *Candida* antigens disclosed herein may be used in antibody capture assays, antigen capture assays, wherein the antigen/antibody complex forms a "special" class of antigen or two-antibody sandwich assays.

Techniques used for Antigen Preparation

The term "*Candida* antigen" as used here means any one of the three separate types of *Candida* antigen utilised in the present invention, namely, cell wall antigen (including mannose), total cytoplasmic antigen (mannose depleted) or purified immunodominant antigen (enolase). Use of the term "*Candida* antigens" means that all three antigens were involved or could be utilised. A number of techniques may be used to prepare the *Candida* antigens including biochemical extraction, column chromatography, Gel fractionation, gene cloning, differential precipitation, filtration, dialysis or centrifugation; however, the preferred techniques are those disclosed herein. Briefly, these techniques involve either mechanical, chemical or enzymatic lysis of *Candida* cells, followed by separation of insoluble cell walls from soluble cytoplasmic fraction by centrifugation, filtration and dialysis. Chemical treatment of cell wall fraction to release cell wall antigens followed by centrifugation and dialysis. Filtration and organic extraction of soluble cytoplasmic cell extract. Separation of mannoproteins by ConA affinity chromatography. Purification of the immunodominant enolase antigen from the soluble cytoplasmic extract by anion and cation affinity chromatography. It will be appreciated by those skilled in the art that other techniques, or modifications or variations of the above techniques, may be adopted without adversely affecting the spirit of the present invention.

Techniques used for Antibody Preparation and Labelling

Antiserum to the *Candida* antigens disclosed herein may be produced in a host animal such as rabbit or sheep. The serum fraction containing the antibody may be isolated by standard techniques. This antiserum may be employed in several of the embodiments of the invention hereinafter set forth, or a more sensitive and specific antibody might be obtained by further purification of the serum by electrophoresis, high-speed centrifugation or the like. Ultimately, large quantities of highly specific monoclonal antibody may be produced by means of the hybrid-myeloma techniques by methods known to those skilled in the art.

Certain embodiments of the present invention employ antibody to the *Candida* antigens immobilised on cellulose, agarose, sephadex or glass beads or other similar inert surfaces such as metal, plastic or ceramic which do not interfere with subsequent reaction. Adsorption, Br—CN activation or other techniques known in the art may be employed to immobilise the antibody.

Other embodiments of the present invention employ the antibody to the *Candida* antigens conjugated to a chromophoric (highly coloured) molecule, an enzochromic (an enzyme which produces colour upon addition of reagents) molecule, fluorochromic (fluorescent) molecule or a luminogenic (luminescent) molecule.

The conjugate of antibody with enzyme is made using techniques known in the prior art. (For references, see Avrameas, S. and Uriel, J., in Comptes Rendus Hebdomadaires des Seances de l'Academie des Sciences, vol. 262, p. 2543, (1966); Nakane, P. K. and Pierce, G. B., in Journal of Histochemistry and Cytochemistry, vol. 14, p. 929, (1966); Nakane, P. K., in Methods in Enzymology, vol. 37, p. 133, (1975)).

Chormporic molecules that may be used are 2,3-diriitrobenzene (DNB) salts, dinitrophenol (DNP) and methyl and butyl orange. Other suitable chromophoric agents are well known in the art. Enzochromic molecules that may be conjugated with the antibody are enzymes that give colour with appropriate reagents. Examples are alkaline phosphatase (ALP) which develops colour with nitrophenyl phosphate (NPP), glucose oxidase with glucose, and D-galactopyranoside. These and other examples are well known in the art. Examples of dinitrofluorobenzene and "pipsyl" derivatives. Luminogenic molecules may be conjugated to antibodies by the method of Branchini, et al. (Biochem. Biophys. Res. Commun. 97, 334 (1980)). The term "chromophoric" hereinafter is intended to include "enzochromic", "fluorochromic" and "luminogenic" molecules as well.

Certain embodiments of the invention also utilise *Candida* antibody tagged with a radioactive element. $I^{125}$ conjugated by means of the chloramine-T procedure is a common example, but other methods known in the art may also be employed.

Techniques used for Antigen Immobilisation and Labelling

Antigen molecules may be immobilised on a solid carrier by a variety of methods known in the art, including covalent coupling, direct adsorption, physical entrapment and attachment to a protein-coated surface. For references describing the methodology, see Silman, I. H. and Katchalski, E. in Annual Review of Biochemistry, Vol. 35, p. 873 (1966); Melrose, G. J. H., in Review of Pure and Applied Chemistry, Vol. 21, p. 83, (1971); and Cuatrecasas, P. and Anfinsen, C. B., in Methods in Enzymology, Vol. 22, (1971).

Lai et al. (German OS No. 2,539,657, U.S. Pat. No. 4,066,512) discloses a method of attachment to a protein-coated surface. In this method, the internal and external surfaces of a microporous membrane are first coated with a water-insoluble protein such as zein, collagen, fibrinogen, keratin, glutelin, polyisoleucine, polytryptophan, polyphenylalanine, polytyrosine, or copolymers of leucine with p-amino phenylalanine. Such a coating renders the membrane capable of immobilising a wide variety of biologically active proteins including enzymes, antigens, and antibodies. A microporous structure is defined as one having more than 50% of its total volume in the form of pores ranging in size from 25 nanometres to 25 micrometers, preferably from 25 nanometres to 14 micrometers. A pore size range from 25 nanometres to 5 micrometers is employed in most applications herein. Uncoated microporous membranes have as much as 70 to 75% of their volume as pore space. The pores permit liquid flow through the membrane. After being coated by zein, for example, the pore space is reduced 5 to 10% with the result that the structure retains its essential properties of having a high proportion of its volume as pore space and permitting liquid flow through the pores. The structure has a large surface area in contact with any solution contained within the pores.

Such a coated membrane, having immobilised antigen or antibody, provides a compact, easy to manipulate carrier for the immobilised antigen or antibody. Its integral structure permits removal of bound from unbound components by simple mechanical means.

Non-specific binding may be minimised by interposing a second stage immobilisation step, in which an immunochemically neutral protein is immobilised to the filter. Immobilisation therefore occurs in two stages according to a preferred embodiment of the invention: a first stage in which the desired immunochemical component is immobilised, and a second stage, following the completion of the first, in which an immunochemically neutral protein such as fetal calf serum or bovine gamma globulin is next immobilised. The term immunochemically neutral is defined in terms of the specific components of the assay. Any protein, which does not combine immunochemically with a component of the assay or with one of the reagents, is considered immunochemically neutral, even though such protein might be immunochemically reactive in another system.

Where the substance to be detected is an antibody, the immunochemically reactive moiety of the conjugate must be an antibody capable of binding immunochemically with the antibody to be tested. Such antibodies may be obtained by immunising an animal with the antibody or immunoglobulin fraction of serum from the animal in which the antibody to be tested originated. For example, where the antibody to be tested is a human antibody, a goat antibody against human antibody is obtained from the serum of a goat immunised against human imnmunoglobulin (antibody). The enzyme moiety may be any enzyme capable of catalysing a reaction which can be detected by any method known to those skilled in the art, and which retains its activity after conjugation with antibody. Horseradish peroxidase is preferred because of its convenience and suitability to a wide range of applications. It is well known that the enzyme catalyses the oxidations of a variety of organic compounds in the presence of hydrogen peroxide. Many such organic substrates are chromogenic, ie. undergo a colour change upon oxidation.

It has been found in the present invention that the purity of the enzyme preparation used in the formation of conjugate has an effect on the degree of non-specific binding. The greater the purity of the enzyme preparation, the less the non-specific binding. In part, the reduction is made possible because, the total amount of conjugate protein required is reduced as the specific activity of the enzyme is increased. The opportunity for non-specific binding is therefore reduced as well. In the preferred embodiment, the use of a highly purified peroxidase preparation has been found to significantly reduce the amount of colour reaction observed in control samples as compared with known positives.

Techniques used for *Candida* Antibody Detection
Antibody Capture Technique

A *Candida* antigen prepared by the techniques disclosed herein is immobilised, preferably on an inert surface such as PVC, paper or a similar bibulous mat. The immobilised *Candida* antigen is then put into contact with ta sample suspected of containing *Candida* antibody. In the case of aqueous samples such as blood or urine, the solution is buffered and ionic salts may be present at optimum concentration for *Candida* antibody-*Candida* antigen interaction. TRIS or borate buffered phosphate at pH 7.5. to 9.0 and ionic strength about 0.010 to 0.5, for example, are suitable buffering agents and ionic salts. The inert surface with *Candida* antigen or *Candida* antigen-*Candida* antibody complex thereon is next putinto contact with antibody to *Candida* antigen conjugated to a chromophormic molecule. Preferably the *Candida* antigen is in solution buffered at pH from about 7.5 to 9.0 and ionic concentration equivalent to about 0.01M to about 0.1M NaCl. After careful rinsing under water or with suitable surfactants such as Tween 20 to remove excess coloured antibody, the inert surface is inspected for colour, fluorescence or luminescence directly or after addition of colour-developing agents. Colour on the inert surface indicates interaction between immobilised *Candida* antigen-*Candida* antibody complex in solution. A control may be run for colour comparison.

This technique may be adapted to clinical use by employing *Candida* antigens tagged with radioactive elements and observing either depletion of activity in solution or uptake on solid support of radioactivity. This embodiment is highly sensitive and rapid and suitable for large numbers of samples.

Enzyme-Linked Immunoassay-ELISA

A solution comprising *Candida* antibody conjugated to enzyme which forms colour with developing reagents and buffer and ionic salts suitable for reaction between *Candida* antigen and the *Candida* antibody is put into contact and allowed to react with *Candida* antigen immobilised, preferably, on an inert surface such as PVC, paper strip or glass bead. The amount of enzochromic conjugated *Candida* antibody is sufficient to saturate about 50% of the reactive sites on the immobilized antibody. The inert surface with antibody-*Candida* antigen enzyme complex is put into contact with buffered sample suspected of containing *Candida*, said sample having an unknown amount of *Candida* antibody. The colour of the resultant immobilised antibody-*Candida* antigen-enzyme complex on the strip after colour developing reagents are added is observed in comparison to a control strip which has not been treated with sample containing *Candida* antibody. Dilution in colour on inert surface treated with sample means presence of *Candida* antibody in the unknown sample.

This method may he adapted for clinical use by contacting samples and immobilised enzyme, preferably in tubes which may be centrifuged and watching developing colour spectrophotometrically. This embodiment is very sensitive and rapid.

Radialimmunodiffusion-Precipitin Reaction

One of the *Candida* antigens is suspended in a softened gelatinous medium such as agar or agarose along with buffers and salts to maintain pH between about 6.0 to 9.0 and ionic strength between about 0.01M to 0.5M for optimal antigen-antibody interaction. The suspending medium of U.S. Pat. No. 4,259,207 is a suitable example. The mixture is spread out to harden on a test plate or, preferably, poured into a disc-shaped container such as an Octolony plate. A small amount of sample is placed on the solidified gel, preferably in a centre well and the plate or disc is allowed to stand preferably covered for a period of hours. Diffusion of sample into the surrounding area occurs during this period. If the *Candida* antibody is present, it reacts with the embedded *Candida* antigen and causes an opaque area in a radial pattern about the point of application of sample. A control can be run for comparison. Calibration of an amount of *Candida* antibody in the sample, if desired, can be obtained by controlling temperature, time and size of sample and comparing the resultant size of radial area with one of known concentration.

Radioimmunoassay

A *Candida* antigen of the present invention is immobilised on an inert surface such as glass beads in a separation column. A portion of *Candida* antigen is conjugated to a radioactive element, preferably $I^{125}$ and allowed to react with the immobilised *Candida* antigen in an amount sufficient to, saturate 50% of the binding sites. The immobilised *Candida* antigen-enzyme complex is put into contact with a sample suspected of containing *Candida* antibody, the sample being buffered between pH 6–9 and containing total ionic salts about 0.05 to 0.5M for optimal reaction conditions for formation of *Candida* antigen-antibody complex.

The *Candida* antibody is eluted from the antigen and the eluant is measured for radioactivity. Loss of activity compared to a control indicates *Candida* antibody in the sample.

Haemagglutination

*Candida* antibody may be assayed through standard haemagglutination techniques with *Candida* antigen to antibody used as sensitising agent.

It is to be understood that methods described hereinabove for assay of *Candida* antibody employing coloured reagents have been presented most specifically for application where neither trained personnel nor sophisticated instruments are available. These methods, however, may be adapted for use in a clinical setting where large numbers of samples are to be assayed by substituting radioactive elements for chromogenic conjugated molecules.

It is also to be understood that the term "colour" is not to be interpreted as being limited to the narrow visible range of the electromagnetic spectrum, but is meant to include wavelengths which may be measured by standard spectrophotographic instruments such as spectrophotometers and absorption and emission colourimeters in both the uv and the ir range.

Although it is contemplated that the methods of the present invention are to be applied to biological fluids themselves, the sensitivity and specificity of the method can be improved by culture of the fluids preferably on medium selective for *Candida* prior to testing.

Sensitivity may also be improved by preliminary treatment of biological samples with lysing agents such as isotonic solution, sound, or lysozyme to release *Candida* antibody into the extracellular environment. U.S. Pat. No. 4,166,765, for example, discloses suitable lysing procedures for biological samples containing bacteria. Any lysing agent may be employed which does not interfere with subsequent enzyme activity.

Assays Embodied in Kit Form

The diagnostic method and means of the present invention may be embodied in the form of a kit for use by individuals for self-diagnosis of *Candida* in the privacy of their homes.

The kit comprises a means for sample collection, the *Candida* antigen to *Candida* antibody and a means for detecting reaction between sample and *Candida* antigen.

In embodiments adapted for clinical use, electrophoretic separation techniques such as isoelectric focusing or zone electrophoresis which ard based on differences of both size and charge distribution between products and reactants may likewise be used to separate products from reactants. Products separated electrophoretically may be detected by characteristic locations compared to standards or may be identified by colour or immunochemically. Resinous beads of charged surfaces may also be used to separate products and reactants.

The means for detecting reaction in the case of immunoassay in a preferred embodiment of the invention is a gelatinous medium in which the *Candida* antigen to antibody is suspended. The gelatinous medium is in a transparent glass or plastic container and comprises buffer and ionic salts for optimal conditions for formation of the *Candida* antigen-antibody complex. Reaction is noted as a transparent area radiating from the central point at which the sample is applied.

The means for detecting reaction in another preferred embodiment comprising immunoassay is the *Candida* antigen to *Candida* antibody conjugated to a chromophore in a sealed, sterile packet along with buffer and ionic salts. For assay, the contents of the packet are diluted with water in a marked tube supplied in the kit. Included also in this embodiment is the antigen to *Candida* antibody immobilised on an inert surface. For assay, the inert surface with immobilised *Candida* antigen is put into contact with sample and then with the solution of chromophore-conjugated *Candida* anti-IgA antibody, protein A or protein G. The inert surface is inspected for colour, which indicates *Candida*.

Although the invention has been described with reference to presently preferred embodiments, it should he understood that various modifications can be made without departing from the spirit of the invention. Moreover, the following examples are offered by way of illustration only and are not intended to limit the invention in any manner. All patent and literature references cited herein are expressly incorporated.

EXAMPLE 1

Preparation of *Candida* Antigen

The following three types of *Candida* antigen were prepared:

1). Cell wall antigen (including mannose);
2). Total cytoplasmic antigen (mannose depleted); and
3). Purified immunodominant antigen (enolase).

A clinical isolate of the *Candida albicans*, was obtained from a patient with vaginal thrush. The identity of the *Candida* species was confirmed with the use of an API® 20C Auxonagram strip (API System S.A., France). The *C. albicans* isolate was designated KEMH5.

200 ml YEPD culture medium (1% yeast extract, 2% peptone, 2% D-glucose) was inoculated with the isolate as a starter culture and incubated for 24 h at 30° C. with aeration. The starter culture was then used to inoculate a 10L YEPD culture incubated under similar conditions in a 23L Bio-Flo Fermenter IV System (New Brunswick Scientific, Edison, N.J.).

The *Candida* culture was harvested from the Bio-Flo fermenter system and separated from culture medium with the use of a Pellicon filtration cassette (Millipore, USA). Concentrated cells were separated from residual medium by centrifugation in 500 ml centrifuge flasks for 15 min at 1,660×g and 4° C. The supernatant was discarded and the pelleted cells were resuspended in protein extraction buffer (20 mM bis-Tris, pH 6.5). The yeast cells were then centrifuged as described previously, resuspended and pooled for further processing.

*Candida* cells were ruptured mechanically with the use of a the use of a DYNOMILL™ (WAB, Switzerland). Milling was continued until 99% cell disruption was obtained. The soluble *Candida* cell extracts were collected and dispensed into 50 ml centrifuge tubes. The extracts were centrifuiged for 12 h at 8,517×g and 4° C. to precipitate insoluble cell walls. The supernatants containing the soluble cytoplasmic antigen fraction were recovered and passed through a 0.45 $\mu$m filter membrane.

The filtrates were then extracted with an equal volume of chilled chloroform. Following centrifugation at 4° C. for 15 min at 1,036×g the upper aqueous phase was aspirated and transferred to a dialysis tube. The soluble cytoplasmic protein fractions were dialysed in column binding buffer (20 mM Tris/HCl, pH 7.4, 0.5M NaCl, 1 mM $MnCl_2.4H_2O$, ,1M $CaCl_2$) for 12 h in preparation for chromatography.

The soluble cytoplasmic antigen fraction was depleted of contaminating soluble cell wall mannoprotein by Con A-Sepharose chromatography. The dialysed cytoplasmic antigen fraction was filtered through a 0.45 $\mu$m filter. 50 ml of the dialysed extract was applied onto a Con A-Sepharose column (2.6×12.5 cm) equilibrated in binding buffer at a flow rate of 4 ml/min. The unbound flow-through fraction (non-glycosylated proteins) was collected. Bound mannoproteins were eluted with 0.5M α-methyl mannoside in binding buffer. This step was performed before the next run and to clean the column before storage.

The soluble cytoplasmic antigen fraction was dialysed overnight against 20 mM Tris.Cl, pH7.4. An estimate of the quantity of protein in solution was performed using the BIO-RAD® (Bradford) microassay procedure in accordance with the manufacturers instructions. A portion of the cytoplasmic antigen extract was analysed by SDS-PAGE.

As shown in FIG. 1 there was a number of major protein bands observed which varyed in size from approx 20 kDa up to approx 60 kDa in size. The major staining bands being at 55 kDa, four bands in the 35 to 45 kDa region, 30 kDa and 20 kDa. This was in stark contrast to the large number of Coomassie blue staining bands in the original crude lysate prior to organic extraction and Con A-Sepharose chromatography.

Purifcation of the enolase antigen was conducted in the same fashion as the soluble *Candida* cytoplasmic antigen except that it was not subjected to Con A-Sepharose chromatography. Instead, following dialysis and filtering through a 0.20 μm syringe filter (cellulose acetate), the filtered extracts were applied to a Pharmacia Biotech XK 50/20 chromatography column packed with Pharmacia Biotech Source 15Q quaternary ammononium anion exchanger (Pharrnacia LKB, Uppsala, Sweden). The column was equilibrated prior to chromatography with column binding buffer 'A' (20 mM bis-Tris, pH 6.5). Anion exchange chromatography of the crude extracts was controlled and recorded using the BIO-RAD® and ECONO® system (Bio-Rad Laboratories, USA). Bound protein was eluted from the column with a salt gradient of buffer 'B' (1M NaCl in buffer 'A', pH 6.5). The recovered fractionated proteins were analysed by an enzyme activity assay.

The active enzyme enolase hydrolyses D(+)2-phosphoglyceric acid (PGA) to phosphoenolpyruvate (PEP). The production of PEP can be monitored by spectrophotometry at 240 nm. 20 μl of protein solution was combined with 1 ml of enolase substrate solution (50 mM Tris-HCl pH 7.4, 2.7 mM magnesium acetate, 1.0 mM EDTA, 1.2 mM D(+)2-phosphoglyceric acid) in a quartz cuvette and the change of absorbance recorded at 1 min intervals. The specific activity was defined as the conversion of 1 μmol of PGA to PEP per mm per mg protein. An estimate of the quantity of protein in solution was performed using the DIO-RAD® (Bradford) microassay procedure.

Eluate fractions containing enolase activity were selected and dialysed for 12 h at 25° C. in hpH$_2$O. The dialysed fractions were recovered and filtered through a 0.20 μm syringe filter. The filtrate was concentrated ten-fold by evaporation under vacuum for 5 h. The concentrated samples were dialysed with binding buffer 'A' (10 mM sodium acetate, pH 4.7) immediately prior to application to a Pharmacia Biotech Mono S HR10/10 chromatography column packed with methyl sulphonate cation exchanger (Pharmacia LKB, Uppsala, Sweden). Cation exchange chromatography performed using the BIO-RAD® Biologic system. Bound protein fractions were eluted from the column with a salt gradient of buffer 'B' (1M NaCl in buffer 'A', pH 4.7). Fractions containing enolase activity were identified by the enzyme activity assay described above.

Figure 2:
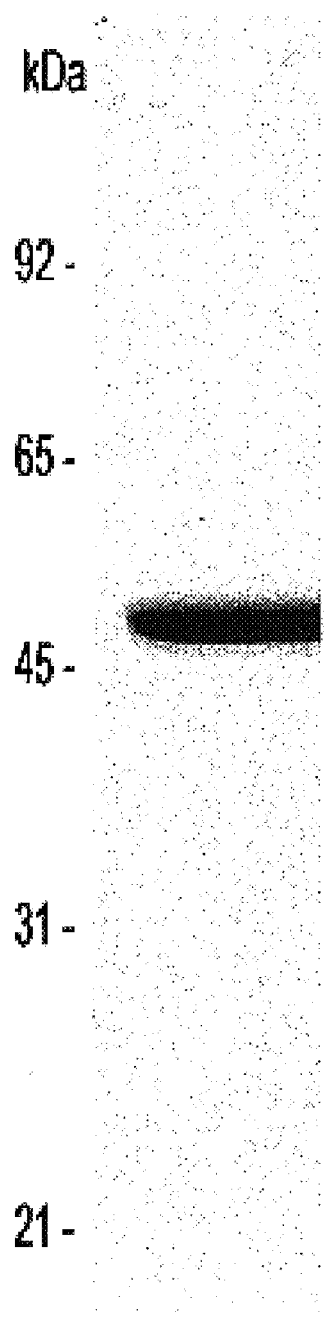
FIG. 2 shows a single coomassie blue band of 48 kDa corresponding to the expected size of the enolase antigen.

FIG. 2 shows a single Coomassie blue band of 48 kDa corresponding to the expected size of the enolase antigen. The identification of the 48 kDa antigen as the glycolytic enzyme enolase was confirmed by an enolase activity assay.

Purification of the cell wall antigen was conducted as follows: the precipitated insoluble cell walls were collected following centrifugation as described above. The cell walls were washed with hpH$_2$O then collected by centrifugation at 6,000 rpm. This step was repeated three times or until the supernatant was no longer cloudy. This ensured any residual soluble cytoplasmic antigen was removed from the cell wall preparation. The washed cell wall pellet was then resuspend in 10 mM Phosphate buffer pH7.4 containing 1% v/v β-Me and incubated for 30 min at 37° C. in a shaker to solubilise the cell wall antigens. The sample was then centrifuged for 5 min at 8,000 rpm and the pellet was then discarded. The supernatant was transferred into a fresh tube and recentrifuged (5 min at 8,000 rpm). The supernatant containing the solubilised cell wall antigen was then dialysed in hpH$_2$O for 48 h at 4° C. (four changes of water), or until no odour was detected. Following dialysis the sample was centrifuged three times 5 min at 8,000 rpm to remove any residual particular matter.

Figure 3:
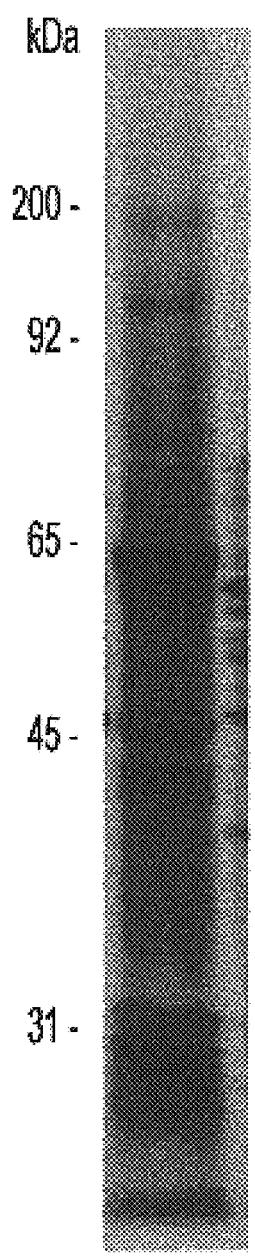
FIG. 3 shows a coomassie blue stained gel of the clarified cell wall antigen preparation. A broad smear of stain can be seen ranging in size from 90 kDa to 200 kDa

Following clarification the cell wall antigen preparation was analysed by SDS-PAGE. The resulting Coomassie blue stained gel is presented in FIG. 3. A broad smear of stain is seen ranging in size from 90 kDa to 200 kDa. The lack of discrete protein bands is typical of mannoproteins, where differences in the number of mannose groups added to the protein base results in a variety of molecular weights.

EXAMPLE 2

Enzyme Linked Immunosorbent Assays (ELISAS)

A serum panel was collected from 1998 to 2000 from various patients with *Candida* infections. Negative control (Control) sera (n=20) were obtained from the Red Cross Blood Bank, Perth, Australia and was obtained from healthy males in the 19 to 25 year age group. Sera (n=13) from patients with recurrent vulvo vaginal candidiasis (VVC) were obtained from King Edward Memorial Hospital, Perth, Australia. Sera (n=108) from patients with oral candidiasis were obtained from Clinipath Ltd and the UWA Dental School, Perth, Australia. Sera (n=39) from patients (n=28) with systemic candidiasis were obtained from Princess Margaret Hospital, Perth, Australia and Prince of Wales Hospital, Sydney, Australia.

In the case of patients with oral and vaginal *Candida* infection, confirmation of infection was made by physical examination and by culture of *Candida* organisms from the relevant body site. In the case of patients with systemic infection, confirmation of infection was through positive blood culture or biopsy. In all cases the immune status of the patient was unknown.

Sera from patients with either superficial or systemic candidiasis were screened by ELISA using trays coated with the *Candida* cytoplasmic antigen. The protein content of each antigen preparation was determined using a commercial assay (BioRad) with BSA as a standard. A series of ELISAs were performed to determine the optimal coating concentration for each antigen (data not shown). The optimal coating concentration being that which gave the greatest discrimination between a positive and a negative control serum. For each antigen the optimum coating concentration was determined to be 2 μg/ml.

A 96 well C8 strip microtitre plate (Greiner GmbH, Germany), was coated with either *Candida* cell wall antigen, cytoplasmic antigen, or purified enolase antigen as prepared in Example 1. 50 µl of a 2.0 µg/ml solution of the antigen was diluted in coating buffer (0.1M NaHCO$_3$, pH 9.3) and added to individual wells. The plates were incubated for 12 h at 4° C. then equilibrated to ambient temperature. After equilibrating the plates to ambient temperature, coating solution was decanted and the plate tapped dried. Plates were inverted on paper towel to drain. Alternatively excess coating solution was aspirated by the automated plate washer (Dynatech Laboratories, Chantilly Va., USA). It was important not to wash the plate at this stage.

A volume of 300 µl of blocking solution (PBS pH 7.3, 2% (w/v) BSA (ICN, Australia), 0.01% (w/v) Tween 20), was applied to each well and incubated at 25° C. for 90 min. Blocking solution was decanted and the plate tapped dried. Plates were inverted on paper towel to drain and tapped dried for a second time. At this stage plates were either used immediately, or dried for storage. Plates to be dried were placed inverted in a sealable container such as a plastic food container with a number of silica gel desiccant sachets for 48 h. The inclusion of approximately 20 small desiccant sachets was adequate for the drying of 6 coated ELISA micro-well trays. Dried plates were sealed into heat-sealed packets with a single desiccant sachet and labelled. Plates were stored at 4° C. until required. Packets containing plates were equilibrated to ambient temperature before opening.

Human test sera diluted 1/100 in blocking solution was dispensed into wells in 50 µl aliquot's and incubated at 37° C. for 30 min. The primary antibody solution was aspirated and wells were washed six times in PBS-Tween 20. The plates were inverted on paper towels and allowed to drain for 10 min. The plates were then tapped dried.

A volume of 100 µl of a horseradish peroxidase anti-human IgG conjugate diluted 1/10,000 in blocking solution was dispensed to each well. Secondary antibody solution was incubated at 37° C. for 30 min. The secondary antibody solution was aspirated and wells were washed six times in PBS-Tween 20. Plates were inverted on paper towel to drain for 10 min and then tapped dried. Plates were inverted on paper towel for a second time and allowed to drain for 5 min. Plates were then tapped dried. Particular care was employed to ensure that all traces of secondary conjugate solution was removed as residual conjugate was established as the major factor responsible for disparity of results (Dynatech Laboratories Inc, USA).

A volume of 100 µl of TMB liquid substrate solution was dispensed into each well and developed at 25° C. for 10 min. The reaction was terminated with the addition of 100 µl of 1M phosphoric acid or 1M H$_2$SO$_4$. The absorbance values for each well were measured at 450 nm, reference 620 nm with a MRX automated plate reader.

Figure 4:
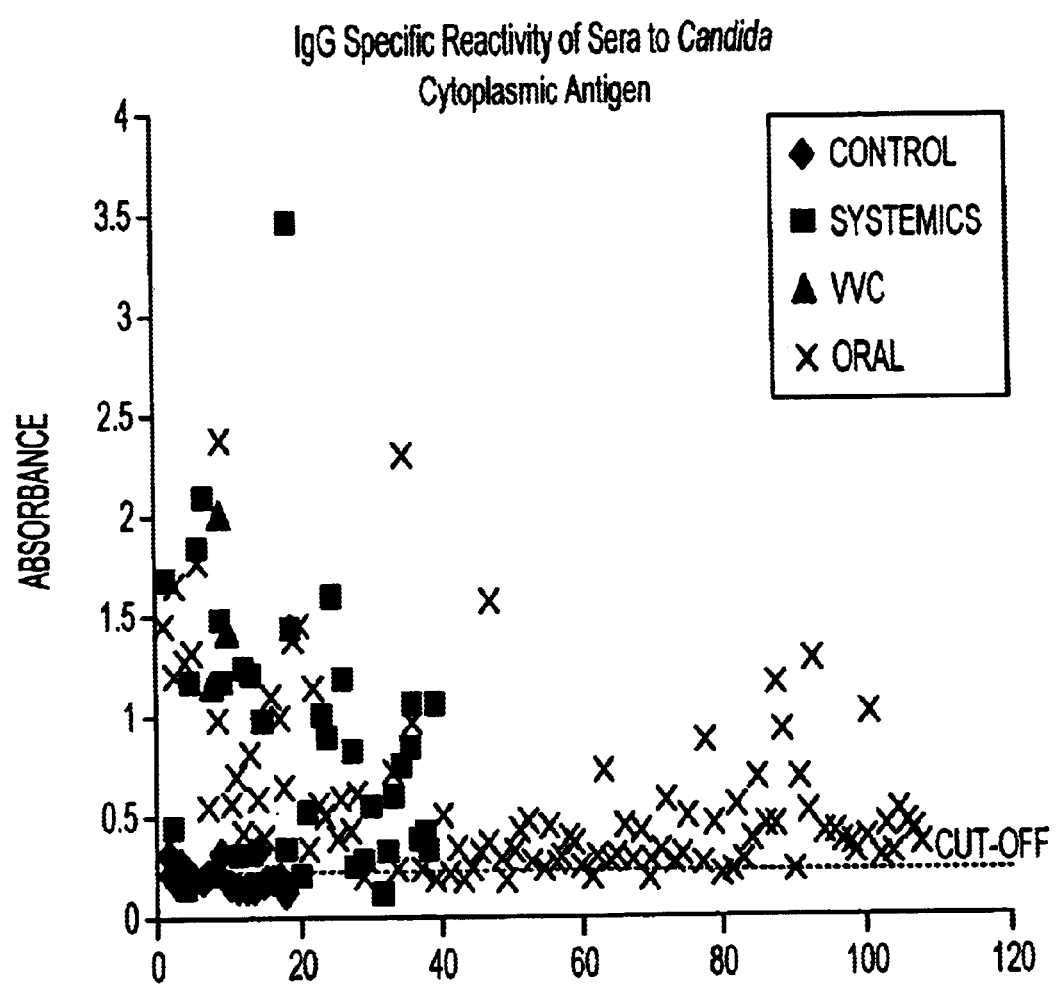
FIG. 4 shows a number of sera screened against the *Candida* cytoplasmic antigen preparation.

Each immunoassay was performed in triplicate and the mean value of absorbance was used. The absorbances are shown as a Scatter diagram in FIG. 4. Three groups of patients with *Candida* infections were analysed. The first group were patients with systemic candidiasis (Systemics), the second group had oral candidiasis (Oral) and the third group had vulvovaginal candidiasis (VVC). Blood bank sera (Control) from males in the 19 to 25 year age group, who were at low risk of having an undetected or subclinical *Candida* infection were used as a control. The cut-off absorbance (OD$_{450}$=0.22) was the mean value of the negative control sera. From these data the cytoplasmic antigen ELISA had a sensitivity of 89% and a specificity of 95%. This is higher than that reported for other *Candida* serological tests (Zoller et al., 1991. J. Clin. Micro. 29:186014 1867).

To further increase the sensitivity of the *Candida* ELISA multiple antigens were used. These were the cell wall, cytoplasmic and native enolase (described above).

Figure 5:
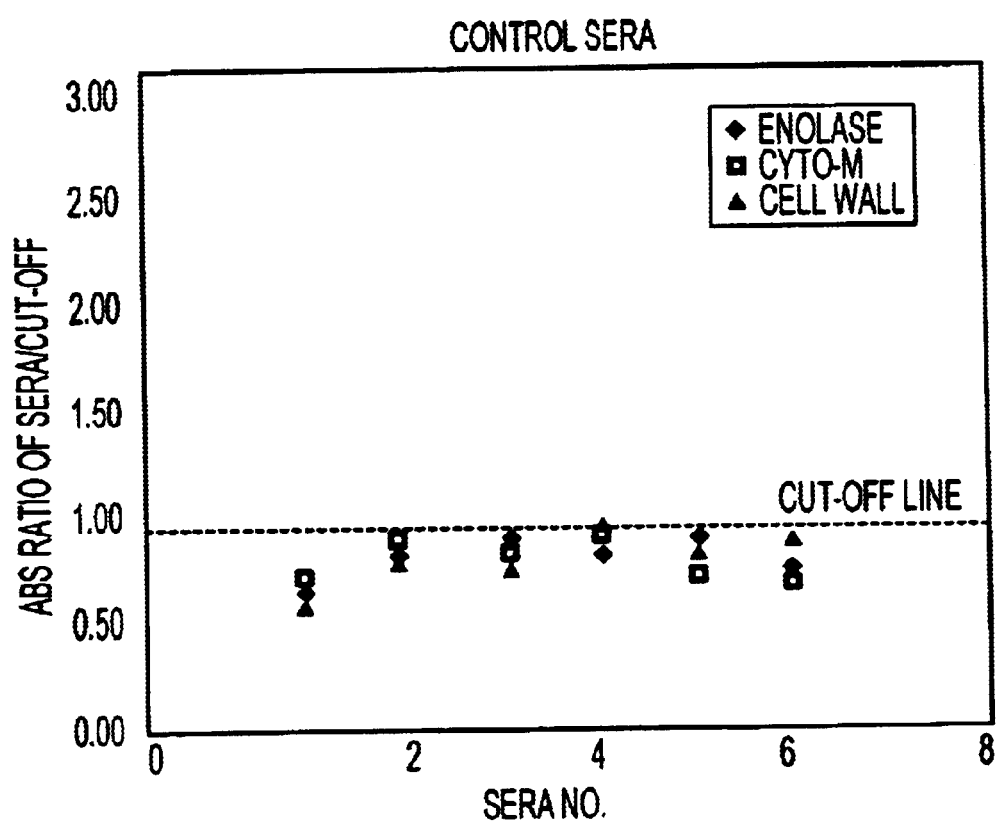
FIG. 5 shows antibody reactivity to the three *Candida* antigens—cytoplasmic, cell wall and immunodominant antigens, using negative control sera.

The use of multiple antigens increased the sensitivity of the *Candida* ELISA. It also provided greater discrimination between superficial and systemic infection. Six negative control sera (serum obtained from healthy males in the 19 to 25 year age group) were used in ELISAs with microtitre tray wells individually coated with the three *Candida* antigens. For each serum the antibody titre to each of the three antigens was below that of the cut-off line (FIG. 5). This line is the cut off value assigned based on a comparison of the average antibody titres of sera from control patients versus those of candidiasis patients. The value plotted on the y-axis of the graph is the ratio of the cut-off absorbance divided into the absorbance of the test serum.

Figure 6:
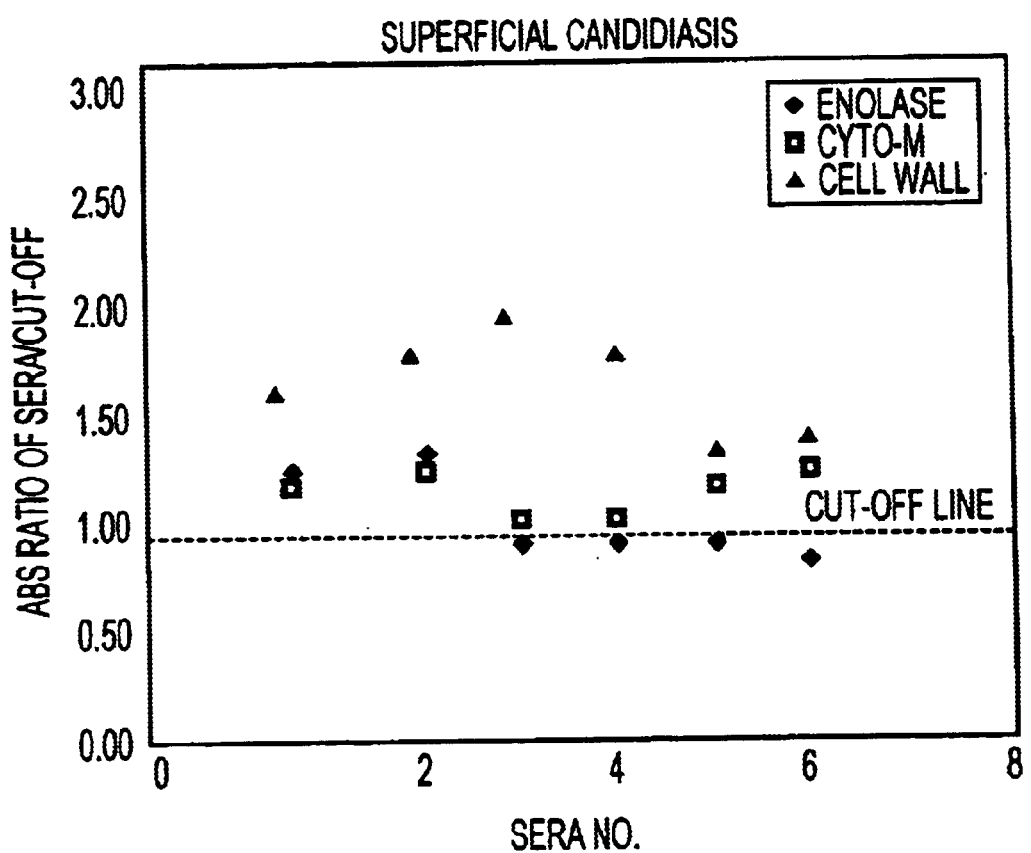
FIG. 6 shows antibody reactivity to the three *Candida* antigens—cytoplasmic, cell wall and immunodominant antigens, using sera from patients with superficial candidiasis.

Serum obtained from 6 patients with superficial candidiasis was then reacted in the ELISA. Again the absorbance value of each serum was divided by the absorbance of the cut-off (FIG. 6). The characteristic antibody response of the sera from patients with superficial candidiasis was a high titre against the cell wall antigen preparation (1.5 to 2 times the cut-off value). The antibody reactivity to the complete cytoplasmic antigen preparation was positive in most cases (1 to 1.5 times the cut-off). In contrast the antibody titre to the enolase antigen was below or equal to that of the cut-off. There is a correlation between the antibody titre to the internal *Candida* antigens (cytoplasmic and enolase) and the severity of the superficial infection (data not shown). However, the severity of the infection in the six patients analysed was not known.

Figure 7:
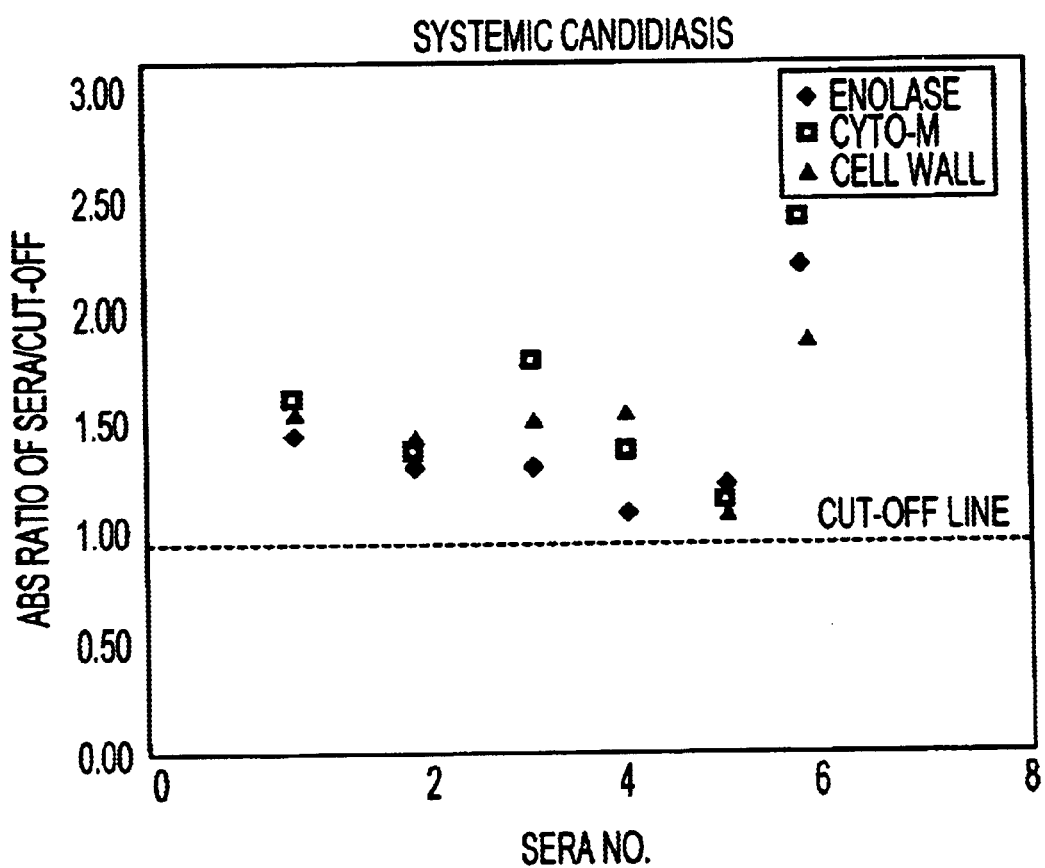
FIG. 7 shows antibody reactivity to the three *Candida* antigens—cytoplasmic, cell wall and immunodominant antigens, using sera from patients with systemic candidiasis.

Six sera taken from patients with systemic candidiasis (confirmed by positive blood culture) were analysed by ELISA. The results are presented in FIG. 7. In the case of the patients with systemic candidiasis the antibody response to the cell wall antigen preparation was positive (1.5 to 2 times the cut-off value). Also, the antibody titres to the internal *Candida* antigens (cytoplasmic and enolase) were also positive (1.5 to 2.5 times cut-off value).

Conclusions

The *Candida* mannan depleted cytoplasmic antigen preparation disclosed herein can be used to identify patients with *Candida* infections. The sensitivity and specificity using an ELISA with microtitre trays coated with this antigen is greater than that obtained by other *Candida* diagnostic tests. Further, the ELISA assay format disclosed herein is easier to perform, more robust and more rapid than formats used in other available *Candida* diagnostic assays. The ELISA format also has the advantage that it is quantifiable. This enables the patient to be monitored over a period of time and changes in the titre of the antibody response to the *Candida* antigens recorded. The ability of the test to monitor overtime the antibody titre to *Candida* antigens has a prognostic value in terns of measuring the patient's response to antifungal drugs and in the overall survival prospects of the patient. Another advantage of the cytoplasmic antigen preparation is that the method developed to produce the antigen is simpler and more rapid than other available procedures (eg. compare with that of Zoller et al., 1991, supra).

What is claimed is:

1. A method of diagnosing *Candida* infection, comprising the steps of:

a) obtaining a biological sample from a subject at risk of, or suspected to be suffering from, *Candida* infection;

b) preparing a composition comprising antigen consisting of a soluble cytoplasmic antigen preparation which is mannose depleted and which consists essentially of *Candida* antigens of molecular weights 55 kDa, 30 kDa and 20 kDa;

c) contacting said antigen composition with said biological sample; and d) using a detection system to deter mine if antibodies from the biological sample are bound to said antigen composition.

2. A method according to claim 1, wherein the antigen composition further comprises one or more antigens selected from the group consisting of cell wall and enolase antigen.

3. A method according to claim 1, wherein step d) is a detection system selected from the group consisting of enzyme-linked immunoassay (ELISA or EIA), biligand binding (sandwich technique), fluorometric assay, chemiluminescent assay, radialimmunodiffusion and radioimmunoassay (RIA).

4. A method according to claim 1, wherein step d) is by ELISA or chemiluminescent assay.

5. A method according to claim 1, further comprising the step of binding the antigen composition to a solid phase either by adsorptive binding, covalent binding, or via a ligand already bound to the solid phase.

6. A method according to claim 1, further comprising the step of using secondary labeled antibodies to detect the antibodies to *Candida* present in the biological samples.

7. A method according to claim 6, further comprising the step of labeling the secondary antibodies with a label selected from the group consisting of fluorescent dye, radioisotope, enzyme, or combinations thereof.

8. A method according to claim 7, wherein the secondary antibody is labeled via bound ligands.

9. A method according to claim 1, wherein detection in the detection system is selected from the group consisting of colour development, chemiluminescence, fluorescence, radioactivity, or combinations thereof.

10. A method according to claim 1, further comprising the step of performing the detection of antibodies by a method selected from the group consisting of qualitative detection, quantitative detection, or combination thereof.

11. A method according to claim 7, further comprising the step of directly labeling the secondary antibody.

12. A method according to claim 7, further comprising the step of indirectly labeling the secondary antibody.

13. A method according to claim 1, wherein the antigen composition is either immobilized on an inert surface, embedded in a gel, or conjugated to a molecule.

14. A method according to claim 13, wherein the molecule imparts colour, fluorescence or radioactivity to the antigen.

15. A method according to claim 1, wherein the biological sample is selected from the group consisting of bone marrow, plasma, spinal fluid, lymph fluid, skin, tears, saliva, milk, blood, serum, blood cells, tumors and organs.

16. A method according to claim 15, wherein the skin consists of external sections selected from the group consisting of respiratory, intestinal, and genitourinary tracts.

17. A method according to claim 14, wherein the biological sample is serum.

18. A kit when used for detecting the presence or absence of a *Candida* antibody in a biological sample, comprising:

a). a biological sample collection device;

b). a composition comprising antigen consisting of a soluble cytoplasmic antigen preparation which is mannose depleted and which consists essentially of antigens for detecting antibodies to *Candida* of molecular weights 55 kDa, 30 kDa and 20 kDa;

c). means for detecting reaction between the antibody in the sample and antigen composition.

19. A kit according to claim 16, further comprising buffering agents and ionic salts.

20. A composition comprising antigen consisting of a soluble cytoplasmic antigen preparation which is mannose depleted and which consists essentially of antigens for detecting antibodies to *Candida* of molecular weights 55 kDa, 30 kDa and 20 kDa.

* * * * *